United States Patent [19]

McCoy

[11] Patent Number: 5,116,737
[45] Date of Patent: May 26, 1992

[54] METHOD FOR GROWING ACID-PRODUCING BACTERIA

[75] Inventor: David R. McCoy, Muskego, Wis.

[73] Assignee: Chr. Hansen's Laboratory, Inc., Milwaukee, Wis.

[21] Appl. No.: 559,185

[22] Filed: Jul. 27, 1990

Related U.S. Application Data

[63] Continuation-in-part of Ser. No. 323,318, Mar. 14, 1989, abandoned.

[51] Int. Cl.$^5$ .................. C12P 39/00; C12P 1/38; A23C 9/12; C12R 1/46

[52] U.S. Cl. ................... 435/42; 435/139; 435/244; 435/245; 435/252.9; 435/253.4; 435/253.6; 435/885; 426/36; 426/38; 426/39; 426/43

[58] Field of Search ............ 435/244, 245, 253.6, 435/885, 139, 253.4, 42, 252.9; 426/36, 38, 39, 43

[56] References Cited

U.S. PATENT DOCUMENTS

| | | | |
|---|---|---|---|
| 4,675,193 | 6/1987 | Boudreaux | 426/43 |
| 4,713,341 | 12/1987 | Bily | 435/252.9 |
| 4,797,289 | 1/1989 | Reddy | 426/43 |

OTHER PUBLICATIONS

Tinson et al. "Austral. J. Dairy Tech" Mar. 1982, p. 14.
Thunell, "pH-Controlled Starter: A Decade Reviewed", Cultured Dairy Products Journal, Aug. 1988, pp. 10-16.
Suzuki, et al., Appl. Environ. Microb. 37:379-382 (1979).
Juillard, V., et al., Can. J. Microbiol., 34:818-822 (1988), with translation.

*Primary Examiner*—Herbert J. Lilling
*Attorney, Agent, or Firm*—Tilton, Fallon, Lungmus & Chestnut

[57] ABSTRACT

A method is disclosed for growth acid-producing bacterial cultures, such as diary cultures, wherein the culture is selected to contain a urease-producing strain of bacteria and the medium used for the culturing contains added urea. During culturing the urease hydrolyzes the urea to acid-neutralizing ammonia which limits the pH drop of the medium, thereby producing cultures of higher bacterial activity. The urea-containing culture media can also be employed with bacterial cultures which do not produce urease, providing urease is added to the culture medium during growth of the bacteria.

8 Claims, No Drawings

METHOD FOR GROWING ACID-PRODUCING BACTERIA

RELATED APPLICATION

This application is a continuation-in-part of co-pending application Ser. No. 323,318, filed Mar. 14, 1989, now abandoned.

FIELD OF INVENTION

The present invention relates to am improved method and composition for growing useful acid-producing bacteria. The bacterial cultures of this invention are adapted for use in producing fermented or cultured food products, or as bacterial additives to human foods or animals feeds.

BACKGROUND OF INVENTION

The practice of adding harmless bacterial to food and feed products is well known. Bacteria are also widely used for producing food products by fermentation processes. Typically, such bacteria are of the genera Lactococcus, Streptococcus. Lactobacillus, Bifidobacterium, Enterococcus, Propionibacterium, Leuconostoc, and Pediococcus, depending on the purpose for which the bacteria are cultured. In recent years, especially in the dairy industry, various compositions commonly referred to as "starter" media have been developed to increase the concentration and/or activity of the bacteria in the cultures produced for use in the food or feed industries. (The term "activity" as used herein designates the rate of acid production per unit volume of a bacterial culture.)

In growing dairy starter culture, pH control has been used commercially. As the bacteria ferment lactose to lactic acid, the buffering capacity of the growth medium is eventually overcome; and then the pH drops until acidic conditions become unfavorable for the continued rapid growth of the bacteria. Harvey, *J. Bact.*, 90:1330 (1965) stated that growth in an environment below pH 5.0 results in reduced enzyme activity and cell reproduction. Moreover, extended storage of bacteria in an acidic environment can result in cell damage, reduction in cellular energy reserves, and a loss of activity by the culture. To compensate for such a loss in activity, increased amounts of culture or extended production times are usually required.

The dairy industry in an earlier procedure reduced acid damage by cooling the medium containing the bacteria before the medium reached an inhibitory pH. By dropping the temperature of the medium, bacterial growth and acid production can be essentially stopped. Compositions or media containing high numbers of bacteria are commonly referred to as "ripened starters". A cold ripened starter can be used over a longer period of time than non-cooled starter. This procedure works but is dependent upon the cheesemaker to cool the starter medium at exactly the right time.

Various other methods have been developed to reduce acid damage to the bacteria and increase activity of starter cultures. One method has been referred to as "external pH control." In commercial practice, external pH control has used an electronic pH meter with pH electrodes, a neutralizer, and pump to control the pH. Typically, a pH electrode and meter monitor the pH of the medium in the bulk starter tank. As the bacteria grow in the medium, the pH of the medium drops. When the pH of the medium reaches a preset point, the pump is activated by the meter and neutralizer is added to the tank raising the pH of the medium. The increase in pH of the medium is sensed by the pH meter and the pump is turned off. This cycle is typically repeated many times before the carbohydrate in the medium is exhausted, or before the lactate concentration becomes inhibitory. Ammonium hydroxide is the most commonly used neutralizer, but ammonia gas has also been used. Concentrated solutions of sodium or potassium hydrox-ide have been experimentally tested, but are not known to be used in industrial practice.

A second known method is referred to as "internal pH control". In this method, buffer salts, which are insoluble at higher pH values, dissolve as the bacteria produce acid with the lowering of the pH of the medium. As the salts dissolve, they increase the buffering capacity of the medium and reduce the rate of the pH drop. Sandine U.S. Reissue Patent No. 32,079 describes methods and compositions to "internally" control media pH. See Thunell, "pH-Controlled Starter: A Decade Reviewed," *Cultured Dairy Products Journal*, August, 1988, pages 10-16).

In external pH control, the acid is neutralized by addition of a base, while in internal pH control the amount of buffer salt is increased by the increasing solubility of the salt as the pH decreases. In an external system, it is not possible to determine the amount of acid produced by the bacteria by titrating with sodium hydroxide to a phenothalein end-point. In an internal pH buffered system, it is possible since the acid is not neutralized.

Reddy, in U.S. Pat. No. 4,622,304, describes a alternative system which can be referred to as "one-step neutralization." (See Thunell, cited above.) In this system, the bacteria are grown until a first predetermined pH or titratable acidity is attained. At that point, a base or basecontaining solution is rapidly added manually to reach a second predetermined pH or titratable acidity. The bacteria are then allowed to continue growing until a third pH or titratable acidity is reached, at which time the medium containing the bacteria is cooled. The bases used are typically solutions of sodium or potassium hydroxide.

The ability of various bacteria to hydrolyze urea by producing an enzyme is known. For example, the Ninth Edition of *Bergey's Manual of Systematic Bacteriology* published in 1986 at page 1421 describes the ability of Bifidobacteria to hydrolyze urea. [See also Suzuki, et al., *Appl. Environ. Microb.*, 37:379–382 (1979).] Tinson, et al., *Austral. J. Dairy Tech.*, March, 1982, page 14, describes the metabolism of *Streptococcus thermophilus*, stating that its growth in skim milk decreased acid production midway through the log phase of growth. It was postulated that this apparent decrease in acid production, as monitored by a decrease in pH, was due to urease hydrolysis of a small amount of urea which was naturally present in the milk. This indigenous urea was present at a very low concentration, viz., 1.7 mM or 0.01% on a wt./wt. basis.

Juillard, V., et al., *Can. J. Microbiol.*, 34:818–822 1988), describes the urease enzyme of *S. thermophilus*. Their study described the effect of temperature, pH, and substrate concentration on the urease activity. Julliard, et al. also found that urease production is strain dependent, viz. some strains produce high levels of urease while other strains produce little or none at all. In their experiments, urea was added to growth media to determine its effect on the stimulation of urease production.

The enzyme urease is produced by a number of bacteria, yeasts, molds, and plants. It is also known by the International Union of Biochemists Number 3.5.1.5. It can be extracted from jack beans, and is commercially used in testing for urea in body fluids. The article by Juillard, et al. (cited above) lists several bacterial sources of urease.

SUMMARY OF THE INVENTION

The present invention comprises particularly a method of growing acid-producing bacterial cultures where the culture contains a urease-producing bacteria. The growth media are characterized by containing urea for hydrolysis by urease. For example, urea is preferably hydrolyzed by urease produced by the bacterial culture as it multiplies. This hydrolysis produces two moles of ammonia and one mole of carbon dioxide per mole of urea. The ammonia produced neutralizes the acid (e.g., lactic acid) prouced in the culturing. With this system, the growth medium can be maintained at a higher pH, thereby producing rapid bacterial culture and high bacterial activity. Urease can be produced in the culture medium by using strains of urease producing bacteria, for example, selected strains of S. thermophilus or Bifidobacterium. When the bacterial strains being cultured do not produce urease, or sufficient urease, the culture can be modified by adding a harmless urease-producing bacteria. Also, if desired, the urease containing culture media of this invention can be used with non-urease producing bacterial cultures by adding urease to the culture medium.

DETAILED DESCRIPTION

The present invention relates to an improved composition and to a method for growing harmless acid-producing bacterial cultures. The compositions are bacterial growth media which include a protein source, a carbohydrate source, a source of vitamins and minerals, and the added urea. An amount of urea is preferably used which will maintain the pH of the growth medium above an inhibitory pH level. The objective is to assure active growth of the bacterial cultures for an optimum period of time. The urea is utilized as a neutralizing agent in the growth medium because it produces two parts of ammonia and one part carbon dioxide upon hydrolysis by urease. The urease is preferably produced by bacteria growing in the medium. The ammonia produced limit the drop in pH in the growth medium. Preferably a pH range is maintained which promotes growth of the bacteria in the medium over a sufficient period of time to complete the fermentation.

Urea is a water-soluble compound. For example, up to about one gram of urea can dissolve in one gram of water at room temperature. A 10% aqueous solution has a pH of about 7.2. Urea may be obtained from number of commercial sources, including, for example, Aldrich Chemical Company, Milwaukee, Wis. In the present invention, it is preferably used in an effective amount to maintain the pH of the medium at a level for sustaining the growth of the culture.

Specific pH ranges that are desirable for the growth of bacteria are variable by the species of bacteria to be grown. The optimum concentration of the urea to be added is dependent upon the specific pH range desired, the buffering capacity of the medium, and the amount of fermentable carbohydrate present. In general, one mole of urea is required for every two moles of acid that are desired to be neutralized.

In practice, the use of urea can be on a similar basis to use of ammonia in an external pH control system. For example, the amount of ammonia required in an external control system can be replaced on the basis of one mole of urea per two moles of ammonia, and this urea hydrolyzes in the presence of urease to form two moles of ammonia. The liquid medium can have from 0.1 to 2.0 weight percent urea, that is, amounts of urea as little as 0.1% can have some beneficial effect in offsetting a pH drop from the acid production, and amounts of urea up to 2.0% may be useful in some fermentations. More typically, however, the preferred amount of urea in the liquid media is in the range from 0.5 to 1.5 weight percent.

Liquid media may contain from about 5 to 20% total solids. In formulating dry media, the amount of urea to be added can range from 1 to 20%, but is preferably in the range from about 5 to 15% urea.

The pH range for the growth medium can be from 4.5 to 9.2, depending on the bacteria being cultured. For example, *Streptococcus thermophilus* can grow in a pH range from about 4.5 to 9.0, but is preferably cultured between about 5.0 to about 8.0. For producing dairy starter cultures, such as for cheese manufacture, it is preferred to maintain the pH above 5.0, such as preferably a pH in the range from 5.4 to 6.5. The addition of the urea should preferably be made so that the pH of the growth medium is maintained in a range for effective growth.

The kind of urease produced by dairy culture bacteria like jackbean urease is "neutral urease" a distinguished from acid-type urease. The enzymatic activity of neutral urease is greatest at pH's around a neutral range (e.g., 6.0 to 8.0). It is therefore preferred to have present in the culture medium sufficient urea to maintain the pH of the medium above 5.0.

Although urease can be added to the culture medium from a commercial source such as jackbean urease, it is not desirable to have active neutral urease present in the culture medium at the start of the fermentation. In preferred embodiments of the method of this invention, there is essentially no urease present at the start of the fermentation. As the culturing progresses, urease-producing bacteria increase in number and elaborate urease into the medium. At the same time, the bacteria being cultured produce acid, usually lactic acid, which tends to progressively reduce the pH. In accordance with the method of this invention, the drop in pH is offset by the action of the urease on the urea in the medium, which results in at least partial neutralization of the acid being produced. If sufficient urease is not produced or if sufficient urea is not present in the medium, the pH may drop so rapidly that it reaches a level which is unfavorable for rapid growth of the bacteria. It is therefore preferred to have sufficient urea present at the start of the fermentation and to incorporate a sufficient amount of the urease producing bacteria to effectively offset the pH drop and maintain the pH of the medium at pH's favorable to rapid growth and high activity of the bacteria. As indicated above, it is in general undesirable to permit the pH to drop below 5.0 and is preferred to maintain the pH at 5.4 and above.

It is known that *S. thermophilus* strains produce urease. For example, the Tinson, et al. reference (cited above) describes TS2 (*S. thermophilus*) as urease positive. The TS2 strain is available from the CSIRO Dairy Research Laboratory, Highett, Victoria, Australia. Other urease producing *S. thermophilus* strains (CNRZ 21 and CNRZ 368) are available from the Institute National de la Recherche Agronomique Laboratorie de Microbiologie, Latiere, 78350 Joux-en-Josas, France. Strains that produce urease are also available from Chr. Hansen's Laboratory, Inc., Milwaukee, Wis., under the trade designations "Italiano" IT-3 or IT-7 (*S. thermophilus* and *L. bulgaricus*), "Redi-Set" CH3 (*S. thermophilus* and *L. bulgaricus*), and STH (*S. thermophilus*). Urease-producing bacterial strains of the genus Bifidobacteria are available from the American Type Culture Collection, Rockville, Md.

Nutrients used in the growth medium are conventional and usually include carbohydrates, nitrogen or amino acid sources, vitamin sources, essential minerals and buffers. The carbohydrates are typically simple sugars which can be fermented by the bacteria. Examples of carbohydrate sources are glucose, sucrose, lactose, fructose, and the carbohydrate components of milk, whey, whey permeate and corn syrup. Nitrogen sources can be yeast or various forms of yeast. Other sources of assimilable amino acids or proteins include tryptone, casein and casein hydrolysates, phytone, peptone, beef extract, whey or whey protein, milk, soy protein or soy protein hydrolysates and pancreatic extract. Required minerals may vary from bacteria to bacteria but generally include trace amounts of metal salts. Vitamin sources may be pure vitamins or include yeast and yeast extracts, malt and malt extracts, pancreatic extract or beef extract. Buffers may include sodium, aluminum, potassium, magnesium or ammonium salts of various acids including phosphoric, citric, ascorbic or acetic. The buffers are added to reduce pH swings during cell growth and neutralization and to reduce phage-proliferation in the medium. Growth media may have many variations which would be obvious to one skilled in the art. While the urea-containing growth media described herein are adapted for practicing the method of this invention in which the bacterial culture contains a urease-producing strain, the media can also be used with other methods in which urease is added to the media. The urease, whether produced in situ or totally or partially added, must be present during the culturing together with the urea to be effective in controlling media pH to a range favorable for rapid growth and high activity.

Urease-producing cultures of *Streptococcus thermophilus* (Hansen's STH 003), and Bifidobacterium (Hansen's - - - ) have been deposited with the U.S. Department of Agriculture, Northern Regional Laboratory, Peoria, Ill. under Accession No. NRRL B-18936 for the *Streptococcus thermophilus* culture, and under NRRL B-18937 for the Bifidobacterium culture. These deposits were made on an unrestricted basis with respect to public availability of the cultures.

The compositions and methods of this invention are further illustrated by the following experimental examples.

EXPERIMENTAL EXAMPLES

Example 1

A bacterial growth medium was prepared by mixing 4.1 grams magnesium sulfate, 2.0 grams nonfat dry milk solids, 16.4 grams diammonium phosphate, 5.8 grams monosodium phosphate, 16 grams yeast extract, 251.4 grams sweet whey, 3.3 grams casein hydrolysate, and 3,200 grams water. A second medium was prepared with the same ingredients as above, however, 15 grams of urea were also added. A third medium was prepared as above but with 30 grams of urea added. The medium was pasteurized at 90° C. for 60 minutes, then cooled to 42° C. The cooled medium was inoculated at the rate of 0.02% with commercial culture "Italiano" IT-3 (Chr. Hansen's Laboratory, Inc., Milwaukee, Wis.). IT-3 is a culture used commercially to make Mozzarellatype cheeses. It is a mixed culture of *S. thermophilus* and *Lactobacillus bulgaricus* in ratios generally of about 3:1 to about 1:3. The strain of *S. thermophilus* is urease-producing. The medium was agitated so that the pH during fermentation could be accurately monitored. At the end of fermentation, an activity test was performed.

Activity was tested by inoculating 99 milliliters of commercial 2% fat milk with 1% ripened starter. Before inoculation, the milk was tempered to 32° C. After inoculation, the milk was held at 32° C. for one hour and then transferred to a water bath at 44° C. The milk was held in the 44° C. bath for an additional three hours, making the total time from inoculation to final testing four hours. pH, titratable acidity (T.A.) and developed acidity (D.A.) were determined. This procedure somewhat duplicates inoculation level, time and temperature profile used to make mozzarella cheese.

Titratable Acidity (T.A.) is the amount of acid in a solution expressed as percent of lacticacid. It is determined by measuring a 9 ml sample into a beaker, adding 0.5 ml of phenophthalein indicator (1% phenolphthalein in 95% ethanol) and titrating with 0.1N sodium hydroxide to the first permanent color change to pink. The T.A. is equal to milliliters of sodium hydroxide divided by 10.

Developed Acidity (D.A.) is the amount of acid produced by bacteria expressed in percent as lactic acid. It is the difference between the titratable acidity of the solution before inoculation with culture and that at the designated time.

The results are summarized in Table A.

TABLE A

| | Media Data | | |
|---|---|---|---|
| Media | 1 | 2 | 3 |
| Urea | 0 | 15 grams | 30 grams |
| Media pH (12 hours) | 3.65 | 4.20 | 5.57 |
| | Activity Data* | | |
| pH | 5.56 | 4.75 | 4.57 |
| T.A. | 0.35 | 0.62 | 0.68 |
| D.A. | 0.20 | 0.47 | 0.53 |

*4th hour values

The increase in activity due to urea is indicated by the increased amount of acid produced by cells from Media 2 and 3 compared to the amount of acid produced by the cells from Medium 1.

Example 2

Growth media were prepared in a similar manner to those used in Example 1. Media 1 and 2 had the same composition as Medium 1 in Example 1. Medium 1 was "one-step" neutralized during incubation. When the medium reached pH 4.6, sufficient potassium hydroxide solution was added to raise the pH to pH 7.0. Incubation was continued until the medium reached pH 4.8 at which time it was cooled. Final pH on the medium was pH 4.7.

Medium 2 was incubated in a fermenter where the pH could be both monitored and controlled. During incubation, the pH controller was set to turn on a neutralizer pump when the medium reached pH 5.40. Ammonium hydroxide (30% NH$_3$) was used as the neutralizer. The medium was cooled when no more ammonia was taken from the reservoir.

Medium 3 was the same as Medium 3 in Example 1. All three media were inoculated at 0.02% with the "Italiano" culture IT-7 (*S. thermophilus* and *L. bulgaricus*), producing urease, and incubated at 42° C. At the end of fermentation, activity tests were performed as in Example 1. The data is summarized in Table B.

TABLE B

| | Media Data | | |
|---|---|---|---|
| Media | 1 | 2 | 3 |
| Neutralization | One-step | pH Control | Self-neutralizing |
| Final Media pH | 4.66 | 5.44 | 5.88 |
| | Activity Data | | |
| pH | 4.65 | 4.60 | 4.37 |
| T.A. | 0.64 | 0.69 | 0.79 |
| D.A. | 0.48 | 0.53 | 0.63 |

The advantage of urea neutralization is evidenced by the higher activity in Medium 3.

Example 3

Two commercial starter media were rehydrated per normal use instructions. Aliquots were then supplemented before pasteurization with 10 grams of urea per liter for comparison to non-supplemented media. The two media used were "Dephage I.S.S.", produced by the Dairyland Food Laboratories Division of Sanofi, Inc., Waukesha, Wis., and "CR Media", produced by the Marshall Products Division of Miles Laboratories, Inc., Elkhart, Ind. After pasteurization, the media were cooled to 42° C. and inoculated with 0.02% "Italiano" culture IT-3, which produces urease. The data is summarized in Table C.

TABLE C

| | Media Data | | | |
|---|---|---|---|---|
| | 1 | 2 | 3 | 4 |
| Media | ISS | ISS | CR | CR |
| Urea | 0 | 10 g/l | 0 | 10 g/l |
| Final Media pH | 3.60 | 6.67 | 3.66 | 4.54 |
| | Activity Data | | | |
| pH | 6.18 | 6.05 | 6.14 | 5.25 |
| T.A. | 0.23 | 0.28 | 0.24 | 0.48 |
| D.A. | 0.07 | 0.12 | 0.08 | 0.32 |

While neither of the commercial media had been developed for urea neutralization, the advantage of using urea with these commercial products is shown by the higher activity of the urea supplemented cultures.

Example 4

One hundred gallons of medium with the same composition as those used in Example 2 as Media 1 and 3 were made. As in Example 2, Medium 1 was one-step neutralized, and Medium 3 was self-neutralized by the urea in the medium. Both media were inoculated with Italiano culture IT-3, producing urease. After incubation, the media were cooled and used to make Mozzarella cheese. Data for this experiment is summarized in Table D.

TABLE D

| Media Data | | |
|---|---|---|
| Media (from Example 2) | 1 | 3 |
| Neutralization | One-Step KOH | Self-Neutralizing Urea |
| Final Media pH | 4.45 | 5.88 |
| | Activity Data | |
| pH | 5.09 | 4.72 |
| T.A. | 0.50 | 0.67 |
| D.A. | 0.33 | 0.50 |
| | Cheese Vat Performance | |
| Vat Number | 7 | 8 |
| Milk Amount | 25,500 lbs. | 25,500 lbs. |
| Milk TA | 0.15 | 0.15 |
| Milk Temperature | 95° F. | 95° F. |
| Starter in | 7:55 a.m. | 8:50 a.m. |
| Set | 8:50 a.m. | 9:45 a.m. |
| Cut time | 9:08 a.m. | 10:00 a.m. |
| TA | 0.14 | 0.15 |
| Steam on | 9:15 a.m. | 10:05 a.m. |
| Steam off | 9:40 a.m. | 10:25 a.m. |
| Cook Temperature | 109° F. | 110° F. |
| TA | 0.15+ | 0.16 |
| Start Drain | 10:10 a.m. | 10:55 a.m. |
| TA | 0.27 | 0.34 |
| Mill | 10:35 a.m. | 11:20 a.m. |
| pH | 5.11 | 5.05 |
| | Summary | |
| Ripen Time | 55 minutes | 55 minutes |
| Make Time (Set to Mill) | 1 hr. 45 min. | 1 hr. 35 min. |
| Mill pH | 5.11 | 5.05 |

The increased activity due to the urea in the starter is shown both by the activity test and its value in cheese production is shown by the vat performance. The vat made with the urea containing media reached a lower pH in a shorter period of time. In practice, the amount of starter put into the vat would probably be reduced (thereby saving part of the starter), so that comparable make times would be achieved rather than making cheese at the faster rate.

Commercial Example

A dry blend of the starter ingredients was made using the following formula:

| A. Ingredient | % by Weight |
|---|---|
| Nonfat Dry Milk | 0.50 |
| Autolyzed Yeast Extract | 7.50 |
| Sweet Whey Powder | 75.00 |
| Casein Hydrolyzate | 1.00 |
| Magnesium Sulfate | 1.00 |
| Diammonium Phosphate | 4.50 |
| Monosodium Phosphate | 1.75 |
| Urea | 8.75 |
| TOTAL | 100.00% |

B. Starter 90 pounds of the above blend was mixed with 770 pounds of water to make 860 pounds of starter. The liquid medium contained about 0.9% urea. The starter was pasteurized at 185° F. for 45 minutes then cooled to 108° F. The starter was then set with one can (130 ml) of commercial culture Italiano IT-3 (Chr. Hansen's Laboratory, Milwaukee, Wis.). The culture contains a mixture of *L. bulgaricus* and a urease producing strain of *S. thermophilus* and is designed for producing Italian-type cheese such as mozzarella. The following data was gathered:

| Time from Set | pH | Titrable Acidity |
| --- | --- | --- |
| 5:15 hrs. | 6.02 | 0.78 |
| 5:40 | 5.92 | 0.85 |
| 6:00 | 5.87 | 0.84 |
| 6:30 | 5.82 | 0.84 |

The data demonstrated that the media was buffered in such a way so as to prevent a harmful pH from being reached. Cheese product data is summarized below.

| Mozzarella Production Data | |
| --- | --- |
| Pounds Milk | 15,000 |
| Pounds Starter | 85 |
| Ripening Time | 35 minutes |
| Coagulant Addition (set) | |
| Titrable Acidity | 0.18 |
| Temperature | 96° F. |
| Coagulum Cut | |
| Time | 15 minutes after set |
| Whey Titrable Acidity | 0.11 |
| Cook | |
| Time Steam On | 45 minutes after set |
| Time Steam Off | 60 minutes after set |
| Temperature | 112° F. |
| Mill | |
| Time | 125 minutes after set |
| Curd pH | 5.22 |
| Whey Titrable Acidity | 0.71 |

The cheese had normal body and flavor characteristics.

I claim:

1. A method of producing a dairy starter culture, from lactic-acid producing bacteria comprising the steps of:
   a) preparing a starter medium comprising a dry mixture of urea and nutrients for the lactic acid-producing bacteria to be cultured, said medium containing urea in an amount of from 1 to 20 percent by weight of the dry medium;
   b) mixing said started medium with water to form a liquid medium in which the bacteria are to be cultured, said liquid medium containing from 0.1 to 2.0 weight percent urea;
   c) inoculating said liquid medium with the lactic-acid producing bacteria, said bacteria including a urease-producing strain selected from stains of *Streptococcus thermophilus* and Bifidobacterium; and
   d) culturing said bacteria in the liquid urea-containing medium with the production of lactic acid and urease, the urea being hydrolyzed to ammonia by the urease and reacting with the lactic acid to offset the pH drop which would otherwise occur, the liquid medium during the culturing being maintained at a pH above 5.0 by means of said urease hydrolysis of urea to ammonia.

2. The method of claim 1 in which said urease-producing strain is a strain of *Streptococcus thermophilus*.

3. The method of claim 1 in which said urease-producing strain is a strain of Bifidobacterium.

4. The method of claim 1, 2, or 3 in which said liquid medium at the start of said culturing contains from 0.5 to 1.5 weight percent urea.

5. The method of claims 1, 2, or 3 in which during said culturing the liquid medium is maintained at a pH of not lower than 5.4 by means of said urease hydrolysis of urea to ammonia.

6. A method of producing a dairy starter culture from lactic-acid producing bacteria comprising the steps of:
   a) preparing a starter medium comprising a dry mixture of urea and nutrients for the lactic acid-producing bacteria to be cultured, said medium containing urea in an amount of from 5 to 15 percent by weight of the dry medium;
   b) mixing said starter medium with water to form a liquid medium in which the bacteria are to be cultured, said liquid containing from 0.5 to 1.5 weight percent urea;
   c) inoculating said liquid medium with the lactic-acid producing bacteria, said bacteria including a urease-producing strain of *Streptococcus thermophilus;* and
   d) culturing said bacteria in the liquid urea-containing medium with the production of lactic acid and urease, the urea being hydrolyzed to ammonia by the urease and reacting with the lactic acid to offset the pH drop which would otherwise occur, the liquid medium during the culturing being maintained at a pH not lower than 5.4 means of said urease hydrolyzed of urea to ammonia.

7. The method of claim 1 or 6 in which said bacteria also includes a non-urease producing strain of lactic acid-producing bacteria.

8. The method of claim 6 in which said bacteria also include a non-urease producing strain of *Lactobacillus bulgaricus*.

* * * * *

UNITED STATES PATENT AND TRADEMARK OFFICE
CERTIFICATE OF CORRECTION

PATENT NO. : 5,116,737
DATED : May 26, 1992
INVENTOR(S) : McCoy

It is certified that error appears in the above-identified patent and that said Letters Patent is hereby corrected as shown below:

Column 2, line 10, correct "hydrox-ide" to --hydroxide--.

Column 2, line 37, correct "basecontaining" to --base containing--.

Column 3, line 21, correct "prouced" to --produced--.

Column 7, line 9, change "incubatedat" to --incubated at--.

Column 10, line 43, after "5.4" insert --by--.

Column 10, line 44, correct "hydrolyzed" to --hydrolysis--.

Signed and Sealed this

Third Day of August, 1993

Attest:

MICHAEL K. KIRK

Attesting Officer

Acting Commissioner of Patents and Trademarks